United States Patent [19]
Hubbell et al.

[11] Patent Number: 5,468,505
[45] Date of Patent: Nov. 21, 1995

[54] LOCAL DELIVERY OF FIBRINOLYSIS ENHANCING AGENTS

[75] Inventors: Jeffrey A. Hubbell; Jennifer L. Hill-West, both of Austin; Randall C. Dunn, Houston, all of Tex.

[73] Assignee: Board of Regents, The University of Texas System, Austin, Tex.

[21] Appl. No.: 165,392

[22] Filed: Dec. 10, 1993

Related U.S. Application Data

[63] Continuation-in-part of Ser. No. 22,687, Mar. 1, 1993, Pat. No. 5,410,016, which is a continuation-in-part of Ser. No. 843,485, Feb. 28, 1992, abandoned.

[51] Int. Cl.$^6$ .......................... C08G 63/08; C08G 67/00; A61K 9/58
[52] U.S. Cl. .......................... 424/484; 424/485; 424/486; 424/487; 424/488; 514/2; 514/21
[58] Field of Search .................................... 424/484, 485, 424/486, 487, 488; 514/2, 21

[56] References Cited

U.S. PATENT DOCUMENTS

| | | | |
|---|---|---|---|
| 4,840,626 | 6/1989 | Linsky et al. | 604/364 |
| 4,889,722 | 12/1989 | Sheffield et al. | 424/450 |
| 5,002,551 | 3/1991 | Linsky et al. | 606/151 |
| 5,007,916 | 4/1991 | Linsky et al. | 606/151 |
| 5,059,189 | 10/1991 | Cilento et al. | 604/307 |
| 5,094,953 | 3/1992 | Anderson et al. | 435/226 |
| 5,126,141 | 6/1992 | Henry | 424/423 |
| 5,134,229 | 7/1992 | Saferstein et al. | 536/56 |
| 5,155,038 | 10/1992 | Eyal et al. | 514/8 |
| 5,185,259 | 2/1993 | Goeddel et al. | 435/226 |
| 5,223,408 | 6/1993 | Goeddel et al. | 435/69.3 |

OTHER PUBLICATIONS

Birkenfeld, A., et al., "The Effect of Urokinase in the Prevention of Intraperitoneal Adhesions; Role of Blood in their Formation," *Annales Chirurgiae et Gynaecologiae*, 72: 246–249 (1983).
Bouckaert, P. X. j. M, et al., "The Impact of Peritoneal Trauma on Intra-Abdominal Fibrinolytic Activity, Adhesion Formation and Early Embryonic Development in a Rabbit Longitudinal Model," *Human Reproduction*, 5:237–241 (1990).
Boyers, S. P., et al., "Reduction of Postoperative Pelvic Adhesions in the Rabbit with Gore-Tex Surgical Membrane," *Fertility and Sterility*, 49(6) 1066–1070 (1988).
Diamond, M. P., "Pathogenesis of Adhesion Formation/Reformation: Application to Reproductive Pelvic Surgery," *Microsurgery*, 8: 103–107 (1987).
Doody, K. J., et al., "Recombinant Tissue Plasminogen Activator Reduces Adhesion Formation in a Rabbit Uterine Horn Model," *Fertility and Sterility*, 51(3) 509–512 (1989).
Drollette, C. M., et al., "Pathophysiology of Pelvic Adhesions: Modern Trends in Preventing Infertility," *J. Reproductive Medicine*, 37(2) 107–122 (1992).
Dunn, R. C., "Tissue–Type Plasminogen Activator and Adhesion Prevention," *Gynecologic Surgery and Adhesion Prevention*, Michael P. Diamond, et al. (editors), Wiley–Liss, Inc. (publishers), 213–220 (1993).
Dunn, R. C., "Adhesions, Adhesiolysis, and Plasminogen Activators," *Assisted Human Reproductive Technology*, E. S. E. Hafez (editors), Hemisphere Publishing Corporation, 130–137 (1991).
Dunn, R. C., et al., "Formation of Adhesions after Surgical Injury and their Prevention with Tissue–Type Plasminogen Activator in a Rabbit Pelvic Model," *Infertility*, 13:103–111 (1990).
Dunn, R. C., et al., "Effect of Varying Days of Tissue Plasminogen Activator Therapy on the Prevention of Postsurgical Adhesions in a Rabbit Model," *J. Surgical Research*, 54: 242–245 (1993).
Dunn, R. C., et al., "Synergistic Effect of Intraperitoneally Administered Calcium Channel Blockade and Recombinant Tissue Plasminogen Activator to Prevent Adhesion Formation in an Animal Model," *Am. J. Obstet. Gynecol.*, 164(5), 1327–1330 (1991).
Evans, D. M., et al., "Dose Dependency and Wound Healing Aspects of the Use of Tissue Plasminogen Activator in the Prevention of Intra–Abdominal Adhesions," *Am. J. Surg.*, 165: 229–232 (1993).
Gervin, A. S., et al., "Serosal Hypofibrinolysis A Cause of Postoperative Adhesions," *Am. J. Surg.*, 125: 80–88 (1973).
Hill–West, J. L., et al., "Prevention of Postoperative Adhesions in the Rat by In Situ Photopolymerization of Bioresorbable Hydrogel Barriers," *Obstetrics and Gynecology* (1994).
Meier, H., et al., "Erste Klinische Ergebnisse der Intraoperativen Adhasionsprophylaxe bei Kindern," *Langenbecks Arch Chir*, 366 (Kongressbericht 1985).
Menzies, D., et al., "The Role of Plasminogen Activator in Adhesion Prevenstion," *Surgery, Gynecology & Obsterics*, 172: 362–366 (1991).
Montz, F. J., et al., "The Ability of Recombinant Tissue Plasminogen Activator to Inhibit Post–Radical Pelvic Surgery Adhesions in the Dog Model," *Am. J. Obstet. Gynecol.* 165(5) 1539–1542 (1991).
Mund–Hoym, S., et al., "Zur Prophylaxe Postoperativer Adhasionen–Eine Tierexperimentelle Studie," *Geburtsh u. Fraunheilk*, 44: 463–467 (1984).

(List continued on next page.)

*Primary Examiner*—Nathan M. Nutter
*Attorney, Agent, or Firm*—Arnall Golden & Gregory

[57] ABSTRACT

A method of preventing adhesions by topical administration of fibrinolysis enhancing agents is described. The method uses a topically applied polymeric matrix for delivery of a fibrinolyic agent, preferably urokinase, or tPA. In the most preferred embodiment, the matrix is extremely thin and is polymerized in situ to form a biodegradable polymeric matrix. The matrix provides controlled release of the agent over a period of time effective to prevent surgical adhesions and is biodegradable, usually within the same time frame. Examples demonstrate that the combination of the matrix and the urokinase or tPA is effective in preventing surgical adhesions.

17 Claims, No Drawings

OTHER PUBLICATIONS

Orita, H., et al., "Inhibition of Postsurgical Adhesions in a Standardized Rabbit Model Intraperitoneal Treatment with Tissue Plasminogen Activator," *Int. J. Fertil.*, 36(3) 172–177 (1991).

Phillips, D. A., et al., "The Effects of a New Tissue Plasminogen Activator Analogue, Fb–Fb–CF, on Cerebral Reperfusion in a Rabbit Embolic Stroke Model," Ann. Neurol., 25: 281–285 (1989).

Rasmussen, H., et al., "Postoperative Intraperitoneale Adhaerenser," *Ugeskr Laeger,* 155(21) 1617–1621 (Mar. 24, 1993).

Rivkind, A. I., et al., "Urokinase Does Not Prevent Abdominal Adhesion Formation in Rats," *Eur. Surg. Res.* 17:254–258 (1985).

Slater, N. D., et al., "Peritoneal Plasminogen Activator Activity After Chronic Exposure to Dialysis Fluid," *Perit. Dial. Int.,* 12(2) 262–263 (1992).

Treutner, K. H. et al, "Postoperative, Intraabdominelle Adhasionen–Ein Neues Standardisiertes und Obiektiviertes Tiermondell und Testung von Substanzen zur Adhasionsprophylaxe," *Langenbecks Arch Chir,* 374: 99–104 (1989).

Verreet, P. R., et al., "Preventing Recurrent Postoperative Adhesions: An Experimental Study in Rats," *Eur. Surg. Res.* 21: 267–273 (1989).

Vipond, M. N., et al., "Peritoneal Fibrinolytic Activity and Intra–Abdominal Adhesions," *The Lancet,* 335: 1120–1122 (1990).

Wiseman, D. M., et al., "Fibrinolytic Drugs Prevent Pericardial Adhesions in the Rabbit," *J. Surg. Res.* 53: 362–368 (1992).

LOCAL DELIVERY OF FIBRINOLYSIS ENHANCING AGENTS

This is a continuation-in-part of U.S. Ser. No. 08/022,687 entitled "Photopolymerizable Biodegradable Hydrogels as Tissue Contacting Materials and Controlled-Release Carriers" filed Mar. 1, 1993 by Jeffrey A. Hubbell, Chandrashekhar P. Pathak, Amarpreet S. Sawhney, Neil P. Desai, and Jennifer L. Hill, and now U.S. Pat. No. 5,410,016, which is a continuation-in-part of U.S. Ser. No. 07/843,485 entitled "Photopolymerizable Biodegradable Hydrogels as Tissue Contacting Materials and Controlled Release Carriers" filed Feb. 28, 1992 by Jeffrey A. Hubbell, Chandrashekhar P. Pathak, and Amarpreet S. Sawhney, now abandoned.

BACKGROUND OF THE INVENTION

This invention is generally in the area of delivery of agents for prevention of surgical adhesions, and specifically involves use of locally formed topical gel systems for controlled delivery of fibrinolysis enhancement agents, especially urokinase, for improved prevention of adhesions.

Adhesions in Surgery

The formation of adhesions, or scar tissue bridges, following surgery, remains a serious complication of many surgical procedures. These include pelvic, abdominal, spinal, tendon, ophthalmic, urinary, thoracic and other procedures. Adhesion formation is believed to occur through a series of events, one of which is the formation of fibrin bridges from a serosanguinous exudate occurring after surgery. The organs are first connected by thin fibrin bridges. Over time, these bridges become populated by cells, which may secrete collagen and otherwise stabilize the bridge. It has been observed that the level of cellular secretion of plasminogen activators, which normally cause the breakdown of fibrin by activating the enzyme plasminogen, can be decreased following injury to tissues. Thus, prevention of the stabilization of such fibrin bridges, and in particular enhancement of natural processes which can remove such bridges before their stabilization into adhesions, is highly desirable in the prevention of adhesions.

Cellular secretion of plasminogen activators, e.g., by the mesothelial cells that line the peritoneum, has been demonstrated by Vipond, et al., "Peritoneal Fibrinolytic Activity and Intra-abdominal Adhesions." *The Lancet*, 335:1120–1122 (1990), to be reduced following injury, leading to the lack of resorption of the fibrin bridges prior to maturation into a scar. In the peritoneal cavity, the particular fibrinolytic reduced in secretion was demonstrated to be tPA and not uPA.

Barrier Methods in Adhesion Prevention:

Several physical barrier methods have been utilized in the prevention of postoperative adhesions. These include sheets of oxidized regenerated cellulose (U.S. Pat. No. 5,007,916 to Linsky and Cunningham; U.S. Pat. No. 5,134,229 to Saferstein, et al.) sheets of expanded polytetrafluoroethylene (Boyers, et al., "Reduction of Postoperative Pelvic Adhesions in the Rabbit with Gore-Tex™ Surgical Membrane." *Fertility and Sterility*, 49:1066–1070 (1988)), thermoreversible hydrogels (U.S. Pat. No. 5,126,141 to Henry), and photopolymerized, resorbable hydrogels (U.S. Ser. No. 08/022,687 entitled "Photopolymerizable Biodegradable Hydrogels as Tissue Contacting Materials and Controlled-Release Carriers" filed Mar. 1, 1993 by Hubbell, et al., to which this application claims priority, the teachings of which are incorporated by reference herein). With the exception of the method of Hubbell, et al., these methods have ranged in usefulness, but in no case do the methods eliminate the formation of postoperative adhesions.

Use of Fibrinolytic enzymes in Prevention of Adhesions.

Various fibrinolysis enhancing agents have been used in attempts to prevent adhesions. Because of their availability and biological suitability, streptokinase (SK), urokinase (UK; also known as urokinase plasminogen activator, uPA), tissue plasminogen activator (tPA), and a modified recombinant tPA (Fb-Fb-CF) have been most widely tested. These agents all work by activation of the enzyme plasminogen, causing it to lyse fibrin. Other substances investigated for removal or prevention of fibrin strands have included proteolytic enzymes, drugs, and clotting inhibitors such as heparin, which tend to prevent deposition of additional fibrin, referred to herein as "fibrinolysis enhancing agents".

Fibrinolytic enzymes have been used in the prevention of postoperative adhesions, as reviewed by Dunn, "Tissue-type Plasminogen Activator and Adhesion Prevention." *Prog. Clin. Biol. Res.* 38:213–220 (1993), and "Adhesion, Adhesiolysis and Plasminogen Activators." *Assisted Human Reproductive Technology*, 13:130–137 (1991).

Tissue Plasminogen Activator (tPA).

Tissue Plasminogen Activator (tPA) has been shown to be of use in the prevention of postoperative adhesions, when delivered by minipump infusion, intraperitoneal injection, and topically. Sheffield describes the topical administration of tPA preferably by injection, but possibly in a phospholipid carrier, a salve or ointment, a polysaccharide composition, a thermoplastic polymeric gel or a hydrogel such as a polyoxyethylene-polyoxypropylene block copolymer, which releases over a period of between three hours up to seven days. Wiseman, et al. (*J. Surg. Res.* 53:362–368, 1991), describes the addition of tPA, a tPA analog, Fb-Fb-CF, and SK, alone or in combination with an absorbable sheet of oxidized regenerated cellulose, Interceed TC7 absorbable adhesion barrier from Ethicon, Inc., Somerville, N.J.

Streptokinase (SK).

Streptokinase (SK), the earliest plasminogen activator to become widely available, has been shown by some investigators to be effective in preventing adhesions and ineffective by others. SK has been shown to be effective in the prevention of postoperative adhesions when delivered by peritoneal injection (Meier, et al. "First Clinical Results of Intraoperative Application of Streptokinase-Streptokinase in Children." *Langenbecks Archiv. für Chirurgie*, 366:191–193 (1985), Treutner, et al. "Postoperative, intraabdominelle Adhäsionen-Ein neues standardisiertes und objektivierties Tiermodell und Testung von Substanzen zur Adhasionsprophylaxe.*" *Lagenbecks Archiv. für Chirurgie*, 374:99–104 (1989)) and ineffective in other studies when similarly delivered (Verreet, et al. "Preventing Recurrent Postoperative Adhesions: An Experimental Study in Rats." *Eur. Surg. Res.*, 21:267–273 (1989)). When delivered as a continuous infusion, it was not effective (Sheffield). When delivered from a degradable polymer matrix, it was somewhat effective (Wiseman, et al.).

Reports on side-effects of tPA differ widely, from none, at effective doses (Menzies and Ellis (Surgery. Gynecol. & Obstet. 172:362–366, 1991), or Sheffield), to severe at effective doses (Wiseman, et al.).

Fb-Fb-CF.

Fb-Fb-CF is a tPA analog (Phillips, et al., "The Effects of a New Tissue Plasminogen Activator Analogue, Fb-Fb-CF, on Cerebral Reperfusion in a Rabbit Embolic Stroke Model." *Annals of Neurology*, 25:281–285 (1989)) and was effective in the prevention of postoperative adhesions when released from a degradable polymer matrix (Wiseman, et al.) (*J. Surg. Res.* 53:362–368, 1992).

Genetic engineering is being applied to generate additional forms of plasminogen activators, plasmin, plasminogen, and other fibrinolytic agents, for example, as described in U.S. Pat. Nos. 5,223,408, 5,185,259, and 5,094,953.

Urokinase Plasminogen Activator (uPA).

The majority of studies with Urokinase Plasminogen Activator (uPA) have not demonstrated usefulness in preventing surgical adhesions. uPA has been investigated in the prevention of adhesions, as reported by Dunn (Chapter 13, p. 130–137, in *Assisted Human Reproductive Technology*, ed. E S E Hafez (Hemisphere Pub., New York, 1991) (1991). An initial study with uPA in several species was not successful. However, a second study by Gervin, et al., "A Cause of Postoperative Adhesions" *Am. J. Surg.* 125:80–88 (1973), did show efficacy. Dogs were treated with an intraperitoneal injection of large amounts of urokinase at the time of surgery. At dosages of 20,000 U/kg, there was allegedly a significant decrease in the formation of ileal adhesions.

However, no subsequent studies have demonstrated efficacy. For example, as reported by Rivkind, et al. "Urokinase Does Not Prevent Abdominal Adhesion Formation in Rats." *Eur. Surg. Res.*, 17:254–258 (1985), who studied the administration of urokinase in dosages between 5,000 and 100,000 U/kg administered intravenously, intraperitoneally, and intragastrically immediately postoperatively and at 48–72 hours post surgery. Moreover, uPA released continuously with minipumps at the site of injury did not reduce adhesions, as reported by Sheffield, et al. Another study in rabbits claimed to show efficacy with abrasion injury to the uterine horns, following administration of 10,000 U/kg urokinase either intraperitoneally or intravenously at the time of surgery and at 24 and 48 hours after surgery, both when blood was added to the peritoneal cavity and without added blood (injury in both cases), Birkenfeld and Schenker "The Effect of Urokinase in the Prevention of Intraperitoneal Adhesions; Role of Blood in Their Formation." *Annales Chirurgiae et Gynaecologiae*, 72:246–249 (1983). Notwithstanding the assertion of efficacy, reference to Table 2 of Birkenfeld and Schenker, shows that comparison between the group "Serosal abrading of the right uterine horn —No treatment" and the group "Serosal abrading of the right uterine horn—Urokinase treatment" demonstrates a difference with a p value of only approximately 0.2. By contrast, the group "Serosal abrading+application of blood on right uterine horn—No treatment" differs from the group "Serosal abrading+application of blood on right uterine horn—Urokinase treatment" with a p value<0.02, both by Chi-squared test. Thus, the treatment with urokinase was effective only with the addition of an unnatural amount of blood.

In summary, uPA has been shown to be effective in the prevention of adhesions in only one study, and it has not been possible to reproduce this observation using normal conditions and normal standards for statistical difference. Efficacy with other fibrinolytic agents has also been mixed, with the best results for tPA being obtained only with repeated or continuous infusion of high dosages, and essentially no efficacy being observed with streptokinase.

The literature in this field is highly equivocal about the utility of any of these agents as reliable, clinically effective means for prevention of surgical adhesions.

It is therefore an object of the present invention to provide a reliable means for locally preventing surgical adhesions using fibrinolytic agents.

It is a further object of the present invention to provide a means for preventing surgical adhesions which is minimally invasive, biodegradable over the same period of time as healing occurs, and simply to use.

It is still another object of the present invention to provide a means for preventing surgical adhesions which uses low dosages of fibrinolytic agents.

SUMMARY OF THE INVENTION

Described herein is a method of preventing adhesions by topical administration of fibrinolysis enhancing agents. In particular, described herein is a method using a local, degradable polymeric release system for the prevention of surgical adhesion using a topically applied polymeric matrix for delivery of a fibrinolyic agent, preferably urokinase, or streptokinase. In the most preferred embodiment, the matrix is extremely thin and is polymerized in situ to form a biodegradable polymeric matrix. The matrix provides controlled release of the agent over a period of time effective to prevent surgical adhesions and is biodegradable, usually within the same time frame. In contrast to prior studies with urokinase administered systemically, the combination of the matrix and the urokinase is effective in preventing surgical adhesions, as shown by comparative examples. The examples also demonstrate efficacy for tissue plasminogen activator (tPA) administered via a controlled release, biodegradable system using low dosages.

DETAILED DESCRIPTION OF THE INVENTION

Disclosed herein are delivery systems for the effective and reliable delivery of fibrinolysis-enhancing agents (FEAs) for the prevention of surgical adhesions.

Fibrinolysis-enhancing agents.

FEAs include agents such as urokinase, streptokinase, and tissue plasminogen activator, and genetically engineered variants thereof, all of which operate by binding to plasminogen and causing it to become proteolytically active against fibrin. FEAs also include thrombolytic agents; proteins directly attacking fibrin, such as proteases, including plasmin or plasminogen; molecules which inactivate a class of proteins which themselves inhibit plasminogen (anti-plasmin inhibitors); heparin and other fibrin-deposition blockers; and other agents having the effect of locally enhancing the dissolution of fibrin, or preventing its deposition.

An effective amount of one or more of these materials are administered topically to an area where adhesions are to be prevented. As used herein, "adhesions" includes surgical or postsurgical adhesions, postinfection adhesions, strictures, scar tissue formation, and related processes. Adhesions can occur in pelvic, abdominal, spinal, tendon, ophthalmic, urinary, thoracic and other procedures.

In the preferred embodiment, the agent is urokinase or tPA, most preferably urokinase.

Dosages of FEAs are determined based on routine optimization from dosages currently in use as delivered systemically or by injection, or dosages that have been reported in the literature. In rats, tPA may be used in doses of 0.03 mg per animal up to doses of 12 mg per animal, in a treatment series; present evidence suggests a preferred range, when administered in a polymeric material, in the range of 1 to 2 mg per dose. Appropriate dosages for humans can be obtained by extrapolation; the above rat dose corresponds to the therapeutic amount normally administered for systemic fibrinolysis after heart attack, and thus may be near the upper end of the range. Urokinase likewise has proved effective at doses suitable for systemic application, about 45,000 International Units in the rat, and lower concentrations may be effective. The required range of streptokinase is likely to be higher than the equivalent of 15,000 IU per rat.

Means for topical administration.

Although a number of methods are known for topical delivery, those which have been discovered to be effective yield controlled release of incorporated FEAs over a period of time required to prevent adhesions from forming. The most effective and requiring least patient compliance are those consisting of a biocompatible biodegradable polymeric matrix which can be applied to the site where adhesions are to be prevented at the time of surgery.

The polymeric matrices should meet the following criteria:

The material should be biocompatible and biodegrade, either by hydrolysis or enzymatic cleavage, over a period of between a day and thirty days, for example, although longer degradation times may be desirable in some cases, as determined by the nature of the adhesions to be prevented and their location. In the abdomen, the preferred period is between one day and one month, preferably two days to two weeks, and most preferably, four days to one week.

The material should be in a form which is either (1) applied as a liquid or a gel, which is then polymerized or crosslinked in situ to provide additional physical integrity or binding to the tissue to be affected, or (2) be conformable and securable to the site where adhesion is to be prevented. These materials are distinguished from materials which are pre-formed before delivery to the site, such as Teflon® membranes, oxidized cellulose cloth, or gelatin sponges. The ungelled polymer may be delivered by any suitable means; the preferred means will vary with the particular situation in which adhesions are to be prevented, or fibrinolysis is to be enhanced. If the operation is conducted with laparoscope or trochar, then a preferred method is to spray an ungelled barrier material, preferably containing the fibrinolysis enhancing agent, onto the site of damage; and then to gel the barrier with light, or by other means suitable to the particular barrier system. If the operation involves an open wound, then it may be advantageous to apply the barrier by syringe or similar means. If the barrier is to be emplaced inside a hollow vessel or lumen, then use of a catheter for delivery may be most appropriate.

The thickness of the polymeric material will be determined by several factors, including the amount of FEA to be delivered, the time during which the FEA is to be delivered, the thickness of the barrier required for mechanical resistance, and similar factors. Within these limits, thinner barriers are preferred, since they will erode more rapidly, and often will be quicker to set, and are less likely to obstruct other organs or biological processes, such as blood flow. In general, the thickness contemplated are in the range of 1 to 500 microns. Ranges of 10 to 100 microns are preferred, and ranges of 20 to 50 microns are most preferred. However, thicker barriers are contemplated if required to contain or deliver the appropriate amount of FEA.

The erodability of the material is subject to control through selection of the composition and the stability of its degradable links. The requirements for stability of the material are that it persist long enough to achieve the desired effect, and that it then erode completely in as short a period as feasible. For the prevention of adhesions in the abdomen, current data suggest that the barrier, and the delivery of the FEA, should continue for at least one day, preferably for two or more, and most preferably for at least four days. In spinal disk surgery, fragmentary evidence suggests that periods of 1 to 2 weeks may be preferable, to prevent post-operative adhesions. It is preferable that the barrier complete its disintegration in less than a month, and more preferably in a shorter period such as two weeks, provided that this period is at least as long as the time required for the therapeutic presence of the FEA.

The material must also not be reactive with the incorporated FEA so as to inhibit their effectiveness, but must serve to control the rate of release of FEA at the size, preferably by diffusional restrictions. Since the time for healing is generally in the range of two weeks, the preferred time for release is in the range of between one day and up to thirty days. Control of diffusion is accomplished by design of pore sizes, relative affinity of the barrier matrix for the FEA, partial insolubility of the FEA, and physical size and shape of the deposited barrier. For short treatment times, of the order of a few days, the simple anticonvective effect of a porous hydrophilic matrix may give sufficient control.

The material may also function to prevent adhesion through properties of the polymer per se, which is cumulative to the action of the FEA. Such materials are described in U.S. Ser. No. 08/022,687 entitled "Photopolymerizable Biodegradable Hydrogels as Tissue Contacting Materials and Controlled-Release Carriers" filed Mar. 1, 1993 by Jeffrey A. Hubbell, Chandrashekhar P. Pathak, Amarpreet S. Sawhney, Neil P. Desai, and Jennifer L. Hill, the teachings of which are incorporated herein. Briefly, polymers are formed from biocompatible, biodegradable, polymerizable and at least substantially water soluble macromers, having at least one water soluble region, at least one region which is biodegradable, usually by hydrolysis, and at least two free radical-polymerizable regions. The regions can, in some embodiments, be both water soluble and biodegradable. The macromers are polymerized by exposure of the polymerizable regions to free radicals generated, for example, by photosensitive chemicals and dyes.

An important aspect of the macromers are that the polymerizable regions are separated by at least one degradable region to facilitate uniform degradation in vivo. There are several variations of these polymers. For example, the polymerizable regions can be attached directly to degradable extensions or indirectly via water soluble nondegradable sections so long as the polymerizable regions are separated by a degradable section. For example, if the macromer contains a simple water soluble region coupled to a degradable region, one polymerizable region may be attached to the water soluble region and the other attached to the degradable extension or region. In another embodiment, the water soluble region forms the central core of the macromer and has at least two degradable regions attached to the core. At least two polymerizable regions are attached to the degradable regions so that, upon degradation, the polymerizable regions, particularly in the polymerized gel form, are separated. Conversely, if the central core of the macromer is formed by a degradable region, at least two water soluble regions can be attached to the core and polymerizable regions attached to each water soluble region. The net result will be the same after gel formation and exposure to in vivo degradation conditions. In still another embodiment, the macromer has a water soluble backbone region and a degradable region affixed to the macromer backbone. At least two polymerizable regions are attached to the degradable regions, so that they are separated upon degradation, resulting in gel product dissolution. In a further embodiment, the macromer backbone is formed of a nondegradable backbone having water soluble regions as branches or grafts attached to the degradable backbone. Two or more polymerizable regions are attached to the water soluble branches or grafts. In another variation, the backbone may be star shaped, which may include a water soluble region, a biodegradable region or a water soluble region which is also biodegradable. In this general embodiment, the star region contains either water soluble or biodegradable branches or grafts with polymerizable regions attached thereto. Again, the photopolymerizable regions must be separated at some point by a degradable region.

Examples of these macromers are PEG-oligolactyl-multiacrylates. The choice of appropriate end caps permits rapid photopolymerization and gelation; acrylates are selected because they can be polymerized using several initiating systems, e.g., an eosin dye, by brief exposure to ultraviolet or visible light. The poly(ethyleneglycol) or PEG central structural unit (core) is selected on the basis of its high hydrophilicity and water solubility, accompanied by excellent biocompatibility. A short poly(α-hydroxy acid), such as polyglycolic acid, is selected as a preferred chain extender because it rapidly degrades by hydrolysis of the ester linkage into glycolic acid, a harmless metabolite. Although highly crystalline polyglycolic acid is insoluble in water and most common organic solvents, the entire macromer is water-soluble and can be rapidly gelled into a biodegradable network while in contact with aqueous tissue fluids. Such networks can be used to entrap and homogeneously disperse water-soluble drugs and enzymes, such as the FEAs, and to deliver them at a controlled rate. Other preferred chain extenders are polylactic acid, polycaprolactone, polyorthoesters, and polyanhydrides. Polypeptides and polysaccharides may also be used.

These materials are particularly useful for controlled drug delivery, especially of hydophilic materials such as most of the FEAs, since the water soluble regions of the polymer enable access of water to the materials entrapped within the polymer. Moreover, it is possible to polymerize the macromer containing the material to be entrapped without exposing the material to organic solvents. Release may occur by diffusion of the material from the polymer prior to degradation and/or by diffusion of the material from the polymer as it degrades, depending upon the characteristic pore sizes within the polymer, which is controlled by the molecular weight between crosslinks and the crosslink density. Deactivation of the entrapped material is reduced due to the immobilizing and protective effect of the gel and catastrophic burst effects associated with other controlled-release systems are avoided. When the entrapped material is an enzyme, the enzyme can be exposed to substrate while the enzyme is entrapped, provided the gel proportions are chosen to allow the substrate to permeate the gel. Degradation of the polymer facilitates eventual controlled release of free macromolecules in vivo by gradual hydrolysis of the terminal ester linkages.

An advantage of these macromers are that they can be polymerized rapidly in an aqueous surrounding. Precisely conforming, semi-permeable, biodegradable films or membranes can thus be formed on tissue in situ. In a particularly preferred embodiment, the macromers are applied to tissue having bound thereto a photoinitiator, and polymerized to form ultrathin coatings. This is especially useful in forming tissue barriers during surgery which thereby prevent adhesions from forming.

Examples in this application demonstrate the use of these macromers and polymers for the prevention of postoperative surgical adhesions in rat cecum and rabbit uterine horn models. The polymers show excellent biocompatibility, as demonstrated by minimal fibrous overgrowth on implanted samples. Hydrogels for the models were gelled in situ from water-soluble precursors by brief exposure to long wavelength ultraviolet (LWUV) light, resulting in formation of an interpenetrating network of the hydrogel with the mucous, serous, or sero-sanguinous layer coating the tissue. The degradable hydrogel was very effective, both by itself and in combination with tPA, in preventing adhesions.

These materials are distinguished from materials such as oxidized regenerated cellulose cloth, or perfluoroalkylene membranes, by their ability to be delivered by syringe, catheter, spray or solution, which enables their delivery to sites of tissue injury through less invasive techniques. Moreover, being biodegradable or bioerodable, they do not require removal. They are distinguished from liposomes, from polymeric adjuvants such as dextran, and from non-firmly gelled polymers such as hyaluronic acid, by their ability to be precisely localized at the site or sites where adhesion prevention is required. This minimizes the dose of FEA required to produce the desired effect.

Alternative polymeric materials include materials which are settable by other mechanisms. These include polymers which set on warming, such as poloxamers (Pluronic® or Butyronic® detergents; block copolymers of polyethylene oxide and polypropylene oxide or polybutylene oxide), or hydroxypropyl methyl cellulose; polymers which gel on cooling, such as gelatin; polymers which can gel on exposure to physiological ions (calcium), such as alginate or chitosan; polymers which gel by other mechanisms, such as redox changes; provided in all cases that the settable polymers are also sufficiently inert and erodible.

The present invention will be further understood by reference to the following non-limiting examples.

EXAMPLE 1

Prevention of adhesions by release of fibrinolytics from hydrogel polymeric matrices.

Efficacy testing was done in the rat, with injury to the uterine horn by electrocautery as described by U.S. Ser. No. 08/022,687, to produce a devascularization and serosal injury. Animals were sacrificed seven days following injury and treatment, and adhesions scored. The incisions were reopened and adhesions were scored for extent and tenacity. Extent of adhesion formation was evaluated by measuring the length of the uterine horn that formed adhesions with itself or with the peritoneal wall or other organs. Tenacity of adhesion was classified as either filmy or fibrous. Filmy adhesions were usually transparent, less strong, and could be freed by hand. The fibrous adhesions were dense, whitish, and usually required sharp instrument dissection to be freed. In cases where only a single filmy adhesion band was evident, a score of 5% was assigned.

Typical samples of the horn were excised for histology and were fixed in a 10% neutral buffered formalin solution. Paraffin sections of the samples were stained using hematoxylin and eosin.

The adhesion score is the % of affected area occupied by the adhesions, with grading of each as being filmy or fibrous.

Sexually mature female rats were prepared for surgery. A midline incision was made in the lower abdominal region under anesthesia with Rompun, Ketamine and Acepromazine anesthetics. The uterine horns were located and the vasculature to both horns was systematically cauterized to induce an ischemic injury. After cauterization, macromer solutions (0.5 ml) were applied along the horn and allowed to coat the surface where the cauterization injury had been induced. After uniform application of the macromer solution was complete, the horns were exposed to a LWUV lamp for 1 min to induce gelation. The procedure was repeated on the reverse side of the horns. The incisions were then closed using a continuous 2-0 VICRYL® in place thereof for the musculoperitoneal layer and a 0 Vicryl (Ethicon) suture for the cutaneous layer. No prophylactic antibiotics were administered. The ischemic injury was made as described and the incision was closed without the application of the precursor; all techniques were identical between the treatment group and the control group.

Controls were used where the same animal model was subjected to surgery without application of the macromer; all surgical techniques were identical between the treatment group and the historical controls.

Animals were treated with a photopolymerized hydrogel barrier, with or without fibrinolytic agents included in the barrier. A viscous sterile 15% solution in phosphate buffered saline (8.0 g/l NaCl, 0.201 g/l KCl, 0.611 g/l $Na_2HPO_4$, 0.191 g/l $KH_2PO_4$, pH 7.4) of polyethylene glycol (M.W. 18,500) which has been chain extended on both ends with a short polyglycolide repeat unit (average number of glycolidyl residues: 10 on each end) and which has been subsequently terminated with an acrylate group was prepared. Initiator needed for the crosslinking reaction, 2,2-dimeethoxy-2-phenyl acetophenone, was added to the macromer solution to achieve an initiator concentration of 900 ppm. A 30 second exposure to a long wave UV lamp (Blak Ray) is sufficient to cause polymerization. The fibrinolytic proteins were mixed in the macromer solutions in the concentrations shown in the footnotes to Table 1.

SK was obtained from Astra Pharmaceutical Products, Westborough, Pa.; tPA from Genentech, South San Francisco, Calif., and urokinase from Abbott Laboratories, North Chicago, Ill. A base dose of 3 tPA mg/ml (net 1,740,000 units) was selected. The equivalent doses for SK (45,000 units) and uPA (15,000 units) were calculated based on the relative doses used to treat myocardial infarction, the primary use of the drugs: dose of agent=(3 mg/ml)×(dose of agent used to treat myocardial infarction)/(dose of tPA used to treat myocardial infarction). Each experimental group consisted of 7 rats.

Results and statistical analyses are shown in Table 1.

TABLE 1

Treatment of Adhesions by Release of Fibrinolytics from Hydrogel Polymer Matrices.

| Group | n | Mean Extent[§],% | Std. Dev., % | Mean Grade |
|---|---|---|---|---|
| Control | 7 | 72 | 15 | 1.7 |
| Gel* | 7 | 22 | 10 | 1.1 |
| Gel + SK† | 7 | 45 | 25 | 1.7 |
| Gel + uPA† | 7 | 6 | 6 | 1.0 |
| Gel + tPA† | 7 | 4 | 3 | 1.0 |

*8KL5, 15% macromer in saline.
†Concentrations of proteins in gel precursor were as follows: SK, 1.2 mg/ml; uPA, 1.8 mg/ml, tPA, 3 mg/ml; 1.5 ml per animal, as described above.
[§]Each group is significantly different than the others by Kruskal-Wallis at c confidence level of 95%, except the Gel + uPA and the Gel + tPA groups.

uPA in solution was ineffective, even over a four-day course of intraperitoneal injection. Solutions of tPA were only somewhat effective, reducing adhesions by about one-third of the control. The barrier gel alone, without FEA, reduced adhesions by about 75% of the control. However, the barrier gel and uPA and tPA reduce adhesions significantly, to 4–6%, or by about a factor of five below the gel only control. The barrier gel alone is more effective than any of the FEAs tested alone, but the combination is strikingly more effective than either.

EXAMPLE 2

Comparison with treatment of adhesions by daily injections with Fibrinolytic agents.

To understand the importance of the degradable polymer controlled release system in the efficacy of uPA, the same total dose of the various fibrinolytic drugs was delivered in the same model over a four day period, with intraperitoneal injection of one-fourth of the total dose daily. Solutions of sterile drugs were made up in sterile HEPES-buffered saline (pH 7.4, 10 mM) at the following concentrations: tPA, 3 mg/ml; uPA, 1.8 mg/ml; SK, 1.2 mg/ml. The adhesion model was performed exactly as described in Example 1. A dose of 0.375 ml was given intraperitoneally immediately after injury prior to closure of the peritoneal cavity. An equal dose was administered on each of the next three days by intraperitoneal injection. Thus, the total dose of each drug was identical to that in the study with the degradable polymeric release system. Control animals received an equal volume of HEPES-buffered saline. Each group consisted of seven animals (one animal died in the SK treatment group in the postoperative period, due to anesthesia complications). Adhesions were scored on the seventh postoperative day, as described in Example 1.

Results and statistical analyses are reported in Table 2.

TABLE 2

Treatment of Adhesions by Daily Injection of Fibrinolytics.

| Group | n | Mean Extent[§], % | Std. Dev., % | Mean Grade |
|---|---|---|---|---|
| Control | 7 | 77 | 16 | 1.6 |
| SK† | 6 | 83 | 13 | 1.7 |
| uPA† | 7 | 78 | 18 | 1.7 |
| tPA† | 7 | 49 | 21 | 1.5 |

†Doses of Proteins were as follows: SK, 1.2 mg/ml, 0.375 ml/dose, 1 dose per day, days 0, 1, 2 and 3; uPA, 1.8 mg/ml, 0.375 ml/dose, 1 dose per day, days 0, 1 and 3; tPA, 3 mg/ml, 0.375 ml/dose, 1 dose per day, days 0, 1. 2 and 3.

[§]The tPA group is significantly different than the others by Kruskal-Wallis at a confidence level of 95%; no other group is significantly different.

The daily injection of tPA was somewhat effective, although much less so than the delivery of tPA from the degradable polymeric system. The daily injection of uPA was not effective. Thus, one may conclude that the drugs alone were not responsible for the efficacy observed in Table 1. Rather, the drug formulation in a controlled release formulation was effective.

The studies in Examples 1 and 2 were performed in a blinded and randomized manner. The surgeon performing the injury was blinded to the grouping of the animals. The surgeon administering the gels was blinded as to the content of the gels, and the surgeon administering the injections was blinded as to the content of the injections. The surgeon performing the scoring of adhesions was blinded as to the grouping of the animals.

Modifications and variations of the present invention, a topical gel delivery system for fibrinolytic agents for prevention of surgical adhesions, will be obvious to those skilled in the art from the foregoing detailed description. Such modifications and variations are intended to come within the scope of the following claims.

We claim:

1. A method for preventing tissue adhesions comprising administering to a site where adhesion is to be prevented an effective amount of a fibrinolytic enhancing agent selected from the group consisting of urokinase, thrombolytic agents, proteases specifically cleaving fibrin, anti-plasmin inhibitors, and fibrin deposition blockers in a topically applied biocompatible, biodegradable polymeric matrix which conforms in situ to the tissue and releases the agent in a controlled manner over a period of between one and thirty days.

2. The method of claim 1 wherein the fibrinolytic enhancing agent is urokinase.

3. The method of claim 1 wherein the polymeric matrix degrades over a period of between one and thirty days.

4. The method of claim 1 wherein the polymeric matrix is applied as a liquid or gel and further solidified in situ.

5. The method of claim 4 wherein the matrix is polymerized on the tissue and binds to the tissue.

6. The method of claim 4 wherein the matrix is crosslinked on the tissue and binds to the tissue.

7. The method of claim 4 wherein the matrix is polymerized by free radical initiation.

8. The method of claim 4 wherein the matrix is solidified by a change in temperature or ionic environment.

9. A composition for preventing tissue adhesions comprising an effective amount to prevent tissue adhesions of a fibrinolytic enhancing agent selected from the group consisting of urokinase, thrombolytic agents, proteases specifically cleaving fibrin, anti-plasmin inhibitors, and fibrin deposition blockers in a topically applied biocompatible, biodegradable polymeric matrix which is applicable as a liquid or gel and is further solidified in situ to conform to the tissue and releases the agent in a controlled manner over a period of between one and thirty days.

10. The composition of claim 9 wherein the fibrinolytic enhancing agent is urokinase.

11. The composition of claim 9 wherein the polymeric matrix degrades over a period of between one and thirty days.

12. A method for preventing tissue adhesions comprising administering to a patient at a site where adhesion is to be prevented an effective amount of urokinase in a biocompatible, biodegradable polymeric matrix which releases the urokinase in a controlled manner over a period of between one and thirty days to prevent adhesions.

13. The method of claim 12 wherein the matrix is topically applied to the site where adhesion is to be prevented.

14. A composition for preventing tissue adhesions comprising as the active agent in preventing adhesions the combination of an effective amount of urokinase and a biocompatible, biodegradable polymeric matrix releasing the urokinase in a controlled manner over a period of between one and thirty days.

15. The composition of claim 14 wherein the composition is a liquid which can be solidified when in contact with tissue.

16. The composition of claim 14 wherein the composition is a suspension of polymeric microparticles.

17. The composition of claim 14 wherein the matrix is a hydrogel.

* * * * *